(12) United States Patent  
Meral et al.

(10) Patent No.: US 11,372,094 B2  
(45) Date of Patent: Jun. 28, 2022

(54) REVERBERATION ARTIFACT CANCELLATION IN ULTRASONIC DIAGNOSTIC IMAGES

(71) Applicant: KONINKLIJKE PHILIPS N.V., Eindhoven (NL)

(72) Inventors: Faik Can Meral, Mansfield, MA (US); Francois Guy Gerard Marie Vignon, Andover, MA (US); Jean-Luc Francois-Marie Robert, Cambridge, MA (US)

(73) Assignee: KONINKLIJKE PHILIPS N.V., Eindhoven (NL)

( * ) Notice: Subject to any disclaimer, the term of this patent is extended or adjusted under 35 U.S.C. 154(b) by 297 days.

(21) Appl. No.: 16/612,389

(22) PCT Filed: May 9, 2018

(86) PCT No.: PCT/EP2018/062158  
§ 371 (c)(1),  
(2) Date: Nov. 10, 2019

(87) PCT Pub. No.: WO2018/206736  
PCT Pub. Date: Nov. 15, 2018

(65) Prior Publication Data  
US 2020/0209371 A1    Jul. 2, 2020

Related U.S. Application Data

(60) Provisional application No. 62/504,681, filed on May 11, 2017.

(51) Int. Cl.  
*G06T 5/00* (2006.01)  
*G01S 7/52* (2006.01)  
(Continued)

(52) U.S. Cl.  
CPC ........ *G01S 7/52077* (2013.01); *A61B 8/5207* (2013.01); *A61B 8/5276* (2013.01);  
(Continued)

(58) Field of Classification Search  
CPC ............. G01S 7/52077; G01S 7/52036; G01S 7/52046; G01S 7/52095; G01S 7/52028;  
(Continued)

(56) References Cited

U.S. PATENT DOCUMENTS 5,245,586 A    9/1993  Hassler  
5,318,033 A    6/1994  Savord  
(Continued)

FOREIGN PATENT DOCUMENTS

| JP | H0984794 A | 3/1997 |
| JP | 2015043824 A | 3/2015 |
| JP | 2015061592 A | 4/2015 |

OTHER PUBLICATIONS

PCT/EP2018/062158 ISR-WO, Jul. 23, 2018, 18 Pages.  
(Continued)

*Primary Examiner* — Jose L Couso

(57) ABSTRACT

An ultrasonic diagnostic imaging system acquires received beams of echo signals produced in response to a plurality of transmit events. The received beams are combined with refocusing to account for differences in receive beam to transmit event locations. The delays and weights used in the refocusing are supplemented with delays and weights which correct for reverberation artifacts. The received echo signals are processed to detect the presence of reverberation artifacts and a simulated transmission of reverberation signal components to virtual point sources in the image field is calculated. This simulation produces the delays and weights used for reverberation signal compensation, or estimated (Continued)

reverberation signals which can be subtracted from received echo signals to reduce reverberation artifacts.

13 Claims, 5 Drawing Sheets

(51) Int. Cl.
*A61B 8/08* (2006.01)
*G01S 15/89* (2006.01)
*G06T 7/00* (2017.01)

(52) U.S. Cl.
CPC ...... *G01S 7/52036* (2013.01); *G01S 7/52046* (2013.01); *G01S 7/52095* (2013.01); *G01S 15/8927* (2013.01); *G06T 5/002* (2013.01); *G06T 7/0012* (2013.01); *G06T 2207/10132* (2013.01); *G06T 2207/30004* (2013.01)

(58) Field of Classification Search
CPC . G01S 15/8927; A61B 8/5207; A61B 8/5276; A61B 8/5269; A61B 2090/378; G06T 5/002; G06T 5/50; G06T 5/00; G06T 7/0012; G06T 2207/10132; G06T 2207/30004; G06T 2207/10016; G06T 2207/20182; G06T 2207/20212; G06T 2207/20024; G06T 2207/20216; G06T 2207/20221; G06T 2207/20224; Y10S 367/901; Y10S 128/901; Y10S 128/916; G06K 9/40; G06K 9/0051; G06K 9/6247; G06V 10/30

See application file for complete search history.

(56) References Cited

U.S. PATENT DOCUMENTS

| | | | | |
|---|---|---|---|---|
| 5,348,013 | A * | 9/1994 | Kanda | A61B 8/14 600/443 |
| 6,648,824 | B2 * | 11/2003 | Hwang | G01S 7/52046 600/437 |
| 6,695,783 | B2 | 2/2004 | Henderson et al. | |
| 8,137,272 | B2 | 3/2012 | Cooley et al. | |
| 8,391,504 | B1 | 3/2013 | Abel et al. | |
| 10,231,712 | B2 * | 3/2019 | Ebbini | A61B 8/00 |
| 11,076,836 | B2 * | 8/2021 | Ebbini | G01S 15/8915 |
| 2003/0199763 | A1 | 10/2003 | Angelsen et al. | |
| 2007/0239001 | A1 * | 10/2007 | Mehi | G01S 15/8927 600/437 |
| 2009/0069693 | A1 | 3/2009 | Burcher et al. | |
| 2009/0304246 | A1 * | 12/2009 | Walker | G06K 9/0051 382/128 |
| 2011/0082372 | A1 * | 4/2011 | Tateyama | A61B 8/0833 600/443 |
| 2013/0343627 | A1 | 12/2013 | Zwirn | |
| 2014/0121502 | A1 | 5/2014 | Vignon et al. | |
| 2014/0150556 | A1 * | 6/2014 | Angelsen | G01S 7/52077 73/627 |
| 2015/0080732 | A1 * | 3/2015 | Yamamoto | A61B 8/5207 600/447 |
| 2015/0327840 | A1 * | 11/2015 | Hirama | A61B 8/5253 600/443 |
| 2016/0074017 | A1 * | 3/2016 | Lee | G01S 7/5202 600/442 |
| 2016/0104267 | A1 * | 4/2016 | Hancock | G01S 7/52077 382/131 |
| 2017/0252007 | A1 * | 9/2017 | Mine | A61B 8/4218 |
| 2017/0333005 | A1 * | 11/2017 | Chen | G01S 7/52077 |
| 2018/0103925 | A1 * | 4/2018 | Kim | A61B 8/4483 |
| 2018/0116631 | A1 * | 5/2018 | Taniguchi | G01S 15/895 |
| 2018/0296191 | A1 * | 10/2018 | Mellema | G01S 15/8915 |
| 2019/0129026 | A1 * | 5/2019 | Sumi | A61B 8/00 |
| 2021/0356434 | A1 * | 11/2021 | Chen | G01N 29/0645 |
| 2022/0031287 | A1 * | 2/2022 | Ebbini | G01S 15/8997 |

OTHER PUBLICATIONS

Brende et al.: "Adaptive Reverberation Noise Delay Estimation for Reverberatin Suppression in Dual Band Ultrasound Imaging": Journal of the Acoustical Society of America, American Institue of Physics for the Acoustical Society of America, vol. 138. No. 5, 2015 , pp. 3341-3351.

Byram: "Ultrasonic Reverberation and Off-Axis Cluter Suppression Using Aperture Domain Signal Decomposition"; /SPIE Medical Imaging, 2013:Ultrasonic Imaging, Tomography, and Therapy, Proc. of SPIE vol. 8675, pp. 86750T-1-86750T-9, (Mar. 2013).

Rau et al: "Methods for Reverberation Suppression Utilizing Dual Frequency Band Maging"; Journal of the Acoustical Society of America, 134, pp. 2313-2325 (2013).

Kay et al: "Identification and Removal of Reverberation in Ultrasound Imaging"; IEEE, 2010, pp. 1675-1680.

Robert et al: "Retrospective Dynamic Transmit With a Limited Number of Multi-Lines"; PR-TN 2006/00165, 2006, 64 Page Document.

* cited by examiner

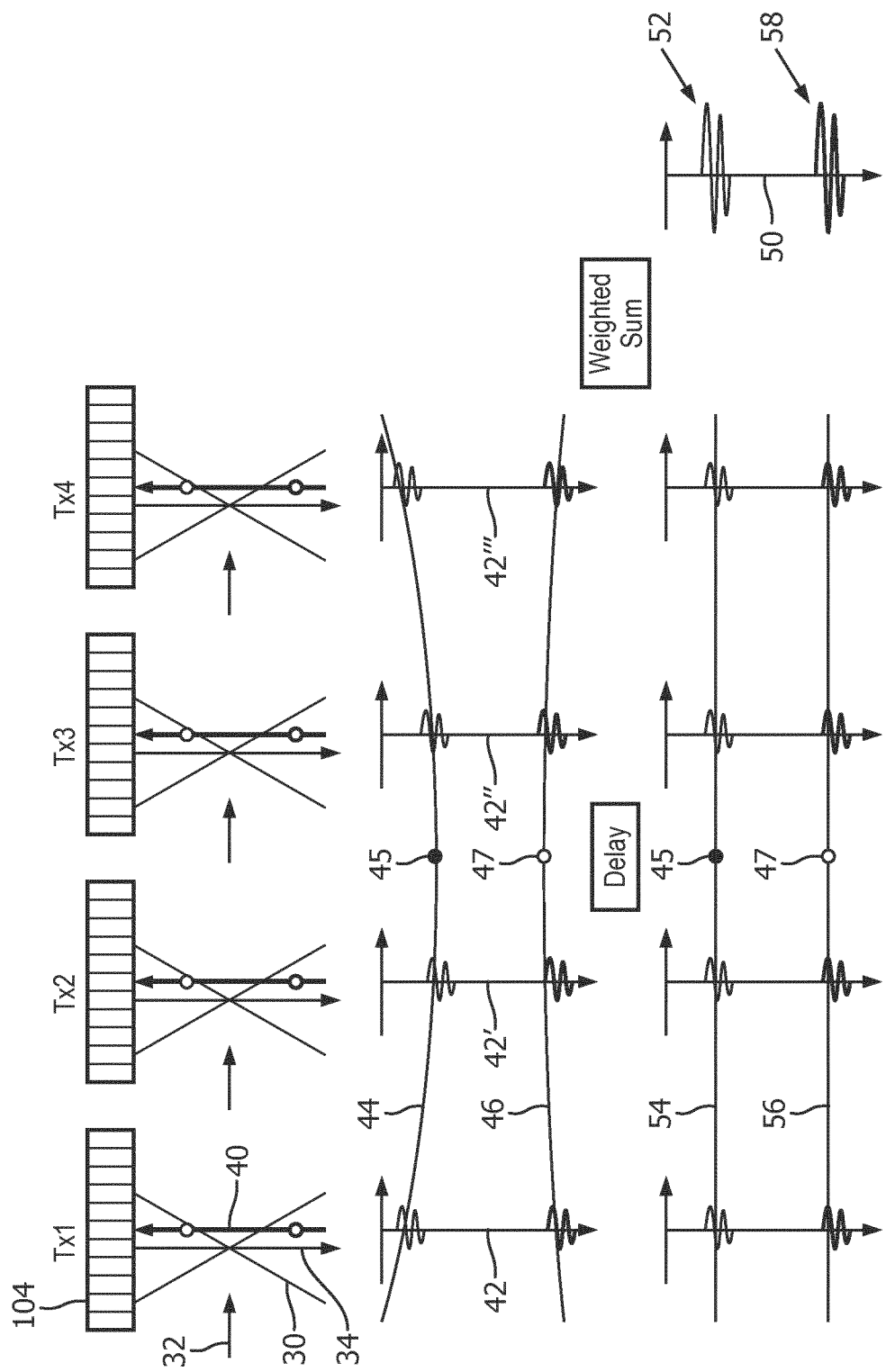

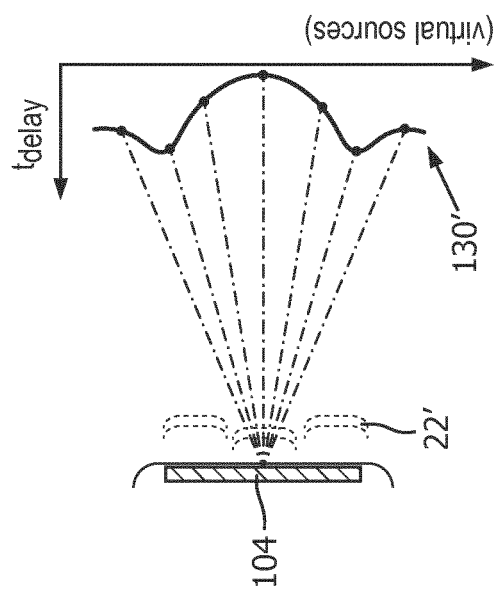
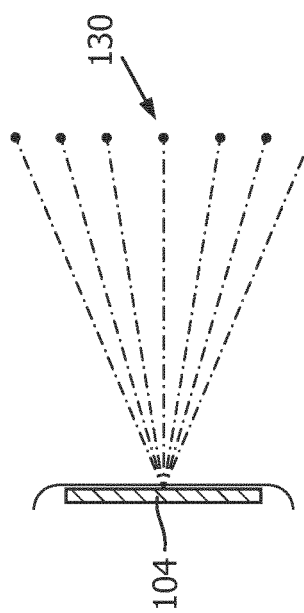
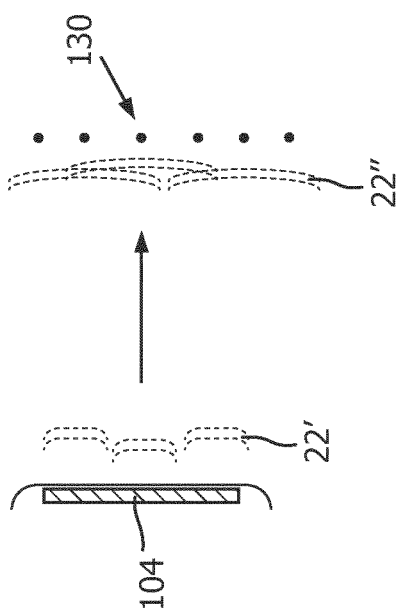

REVERBERATION ARTIFACT CANCELLATION IN ULTRASONIC DIAGNOSTIC IMAGES

CROSS-REFERENCE TO PRIOR APPLICATIONS

This application is the U.S. National Phase application under 35 U.S.C. § 371 of International Application No. PCT/EP2018/062158, filed on May 9, 2018, which claims the benefit of U.S. Provisional Patent Application No. 62/504,681, filed on May 11, 2017. These applications are hereby incorporated by reference herein.

TECHNICAL FIELD

This invention relates to medical diagnostic ultrasound systems and, in particular, to ultrasound systems which reduce or cancel image artifacts due to reverberation echoes in ultrasound images.

BACKGROUND

Medical ultrasound images can become contaminated with image artifacts which originate from various sources. In addition to simple noise artifacts, which can arise when an unsatisfactory signal to noise ratio is extant, other artifacts are particular to phenomena of ultrasound. Speckle artifacts arise by reason of the coherent nature of ultrasound signals. These artifacts, which can appear as a mild watermark in the image, can be reduced by signal processing techniques such as frequency compounding and spatial compounding. Aberration artifacts can arise due to differences in the speed of sound through different tissues and substances in the ultrasound paths to and from the transducer and can be reduced by delay compensation in the beamforming process. Another image artifact which is particular to ultrasound is reverberation artifact. Reverberation occurs when a transmitted ultrasound wave is reflected back by a strong reflector in the near field of the image region and travels back to the face of the transducer, which acts as a reflector to bounce the returning wave outward again, thereby introducing a second outward wave into the image field during echo reception. This reverberated wave will result in its own echo returns which will intermingle with echoes returning from the transmit wave. Although the reverberation echoes are at a lower level than those returning from the transmit wave, they are nonetheless often of sufficient amplitude to produce their own partial phantom image overlaid on the primary desired image.

U.S. Pat. No. 6,905,465 (Angelsen et al.) describes a technique for correcting for reverberation aberrations in ultrasound imaging by transmitting twice, once to sample the returning signals for reverberation signal artifacts, then a second time in which the transmission is adjusted to reduce the effects of reverberation. However, this approach requires two transmit events, which increases the time required to acquire the image data and hence reduces the frame rate of display.

SUMMARY

The present invention aims to desirably reduce or eliminate reverberation artifacts from ultrasound images, without the need for multiple transmissions that reduce the display frame rate.

In accordance with the principles of the present invention, a diagnostic ultrasound system and method are described which reduce the appearance of reverberation artifacts in ultrasound images. The method and system operate by first detecting the presence and location of reverberation artifacts in ultrasound image data by operating on a set of echo signal data. The signal components of the received echo signal data which produce the reverberation artifacts are estimated, preferably using the principles of retrospective dynamic transmit focusing. The estimated reverberation signals are subtracted from the actual received signals, or offsetting phase and weight adjustment used in the beamforming process to reduce or eliminate the reverberation artifacts from the image data used to produce an ultrasound image.

In the drawings:

FIGS. 1 a) through e) illustrate the phenomenon of reverberation artifacts in an ultrasound image.

FIG. 3 illustrates the retrospective dynamic transmit focusing principle.

FIGS. 4 a) through c) illustrate the simulation of a complex wavefront decomposed to virtual point sources in an estimation of reverberation artifact signals.

Figure 1E:
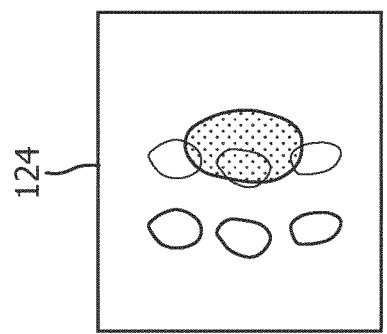
Figure 1B:
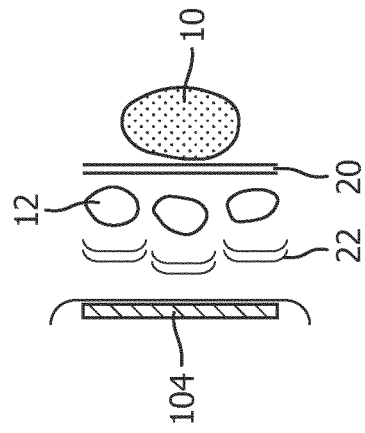
Figure 1D:
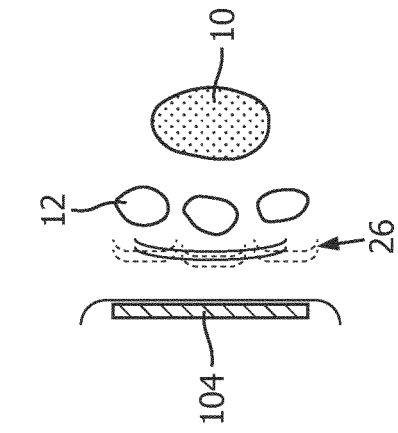
Figure 1A:
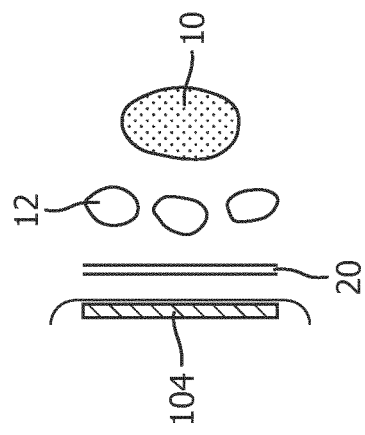
Figure 1C:
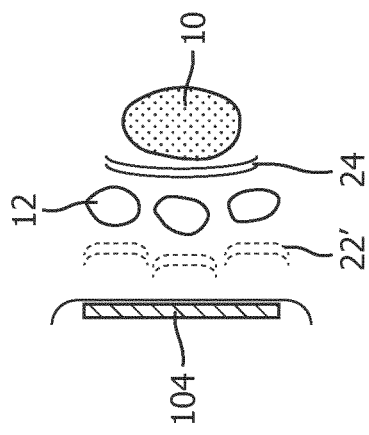
Figure 2:
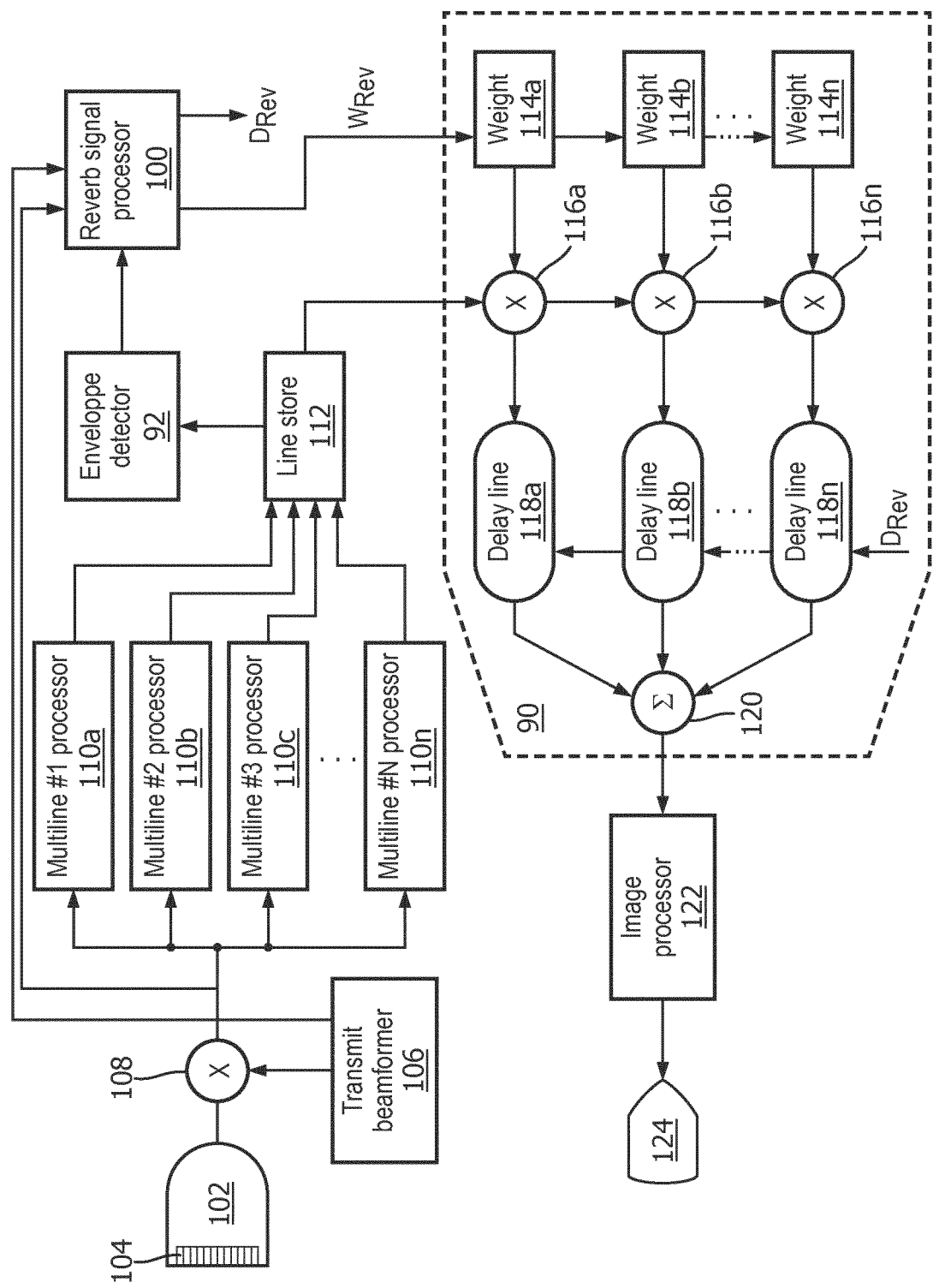
FIG. 2 illustrates in block diagram form an ultrasound system constructed in accordance with the principles of the present invention.
Figure 5:
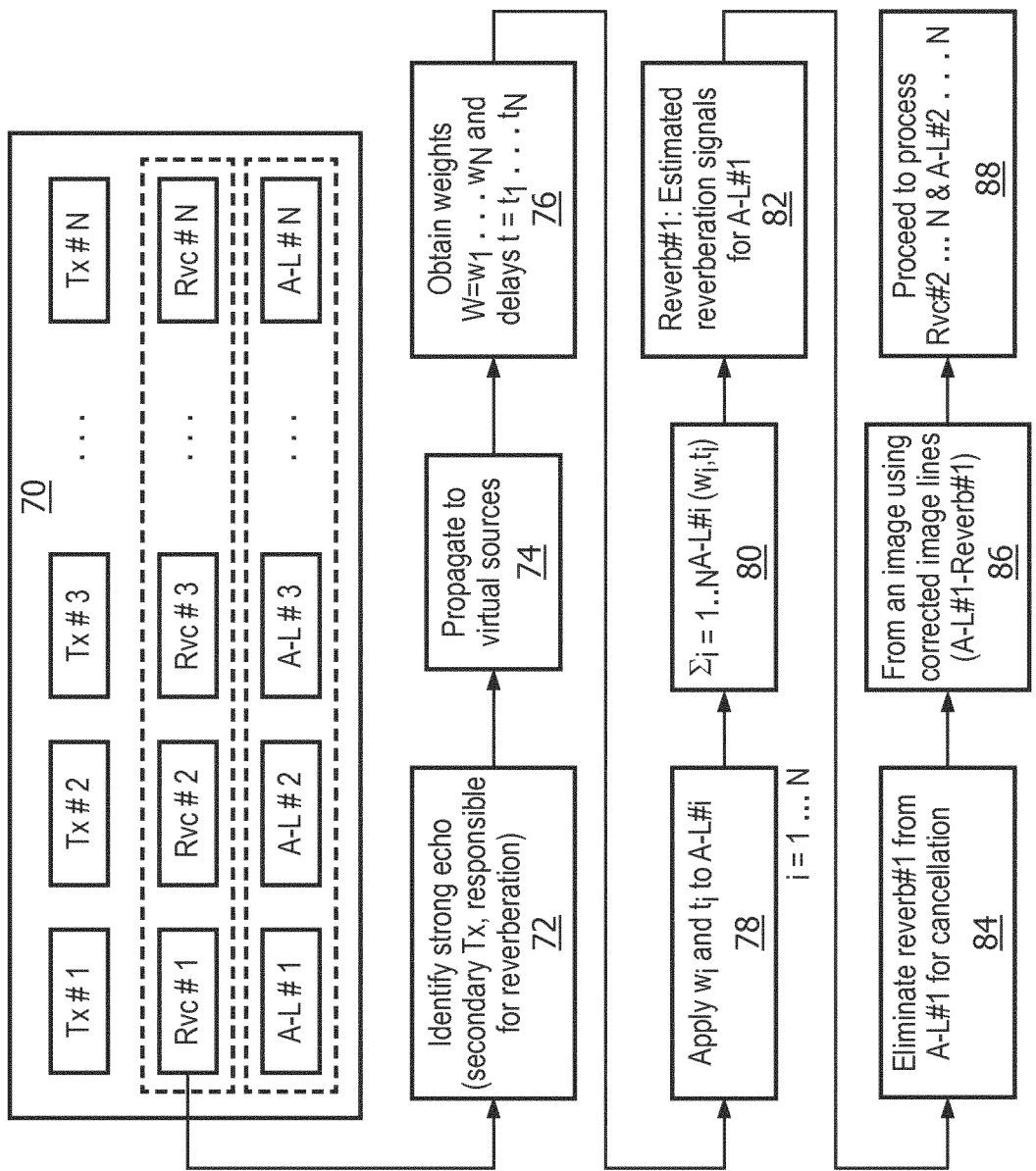

FIG. 5 illustrates the reverberation signal detection and processing performed by the reverberation signal processor of FIG. 2.

The drawings of FIGS. 1 a) through e) illustrate the problem of reverberation artifacts in ultrasound imaging. In FIG. 1 a) a transducer array 104 is shown transmitting a plane wave of ultrasound energy 20 toward a target anatomy 10. In the path between the transducer and the target are a number of specular reflectors 12 which will reflect some of the transmitted ultrasound energy back toward the transducer. These reflectors may be different tissues, bone such as ribs or the skull, air cavities, or other structures which present a significant acoustic impedance discontinuity. FIG. 1 b) shows echoes 22 being reflected back toward the transducer from the reflectors 12. In FIG. 1 c) the echoes 22 have been reflected off of the face of the transducer array 104 and a secondary (reverberation) energy wave 22', mirroring that previously returned by the reflectors 12, now propagates back out through the image field. Meanwhile, the original transmit wave has been reflected back from the target anatomy 10 and echoes therefrom are returning to the transducer array as shown by wavefront 24. When the reverberation energy 22' reaches the reflectors 12 some of the energy is reflected back toward the transducer a second time. These secondary reverberation echoes are shown returning to the transducer array at 26 in FIG. 1 d), where they are intermingled with the echoes returning from the target anatomy. The image produced by these different echoes is shown on screen 124 in FIG. 1 e. The sharp image of the specular reflectors 12 on the left side of the image is constructed from reception of the first set of echoes 22 returned by the reflectors. The image of the target region 10 is constructed from reception of the echoes 24 returned by the target anatomy. But the target anatomy is partially obscured by artifacts of the reverberation echoes returned a second time by reflectors 12 which, by reason of their time of travel that has them intermingling with returning echoes from the target anatomy, produce a reconstructed phantom image which overlays the image of the target anatomy in this example. It is an object of the present invention to detect reverberation echoes and cancel their effects in the image reconstruction, but to do so without using any additional "interrogating" transmissions by the array transducer, which would have the undesirable effect of reducing the frame rate of display of the image.

FIG. 2 illustrates in block diagram form an ultrasound imaging system constructed in accordance with the principles of the present invention. An ultrasound probe 102 includes a transducer array 104 of transducer elements. Selected groups of the transducer elements are actuated at respectively phase delayed times by a transmit beamformer 106 to transmit beams steered and focused at selected focal regions in the desired directions and from the desired origin(s) along the array. The transmit beamformer is coupled to the transducer elements by a transmit/receive switch which may comprise a crosspoint switch that protects the receiver inputs from the high voltage transmit pulses applied. The echoes received by each transducer element of the array 104 in response to each transmit beam are applied to the inputs of multiline processors 110a-110n. Each multiline processor comprises a receive beamformer which applies its own set of delays and, if desired, apodization weights to weight the received echoes from the array elements to form a differently steered and focused receive beam from the same transmit beam. Suitable multiline beamformers for the multiline processors 110a-110n are described, for instance, in U.S. Pat. No. 6,695,783 (Henderson et al.) and U.S. Pat. No. 5,318,033 (Savord). The scanline outputs of the multiline processors 110a-110n are coupled to a line store 112 which stores the received multilines at least until all of the multilines needed to form a scanline of display data have been acquired.

The received multilines are combined by a combiner 90, which performs processing the received signal prior to their scan conversion. The combiner may comprise several units such as multiplier 116, weighting circuits 114, delay 118 and summer 120. The group of multilines used to form a particular line of display data are applied to respective ones of multipliers 116a-116n to produce the display data for the corresponding scanline location. The echo data from each line may, if desired be weighted by apodization weights 114a-114n. In general, these weights will weight each line as a function of its round-trip impulse response. A suitable weighting algorithm can be derived by letting the term amplitude(x,y) be the insonification amplitude of a point at location (x,y) in the image field by the transmit wave-front, the azimuth position x=0 corresponding to the center axis of the transmit beam. Let X be the azimuth of a received multiline with respect to the transmit beam axis. The weight applied to this received multiline to form a point of the image at depth Y is:

$$\text{Weight}(X,Y)=\text{amplitude}(X,Y)$$

For determination of an appropriate delay characteristic, let propagation_time(x,y) be the propagation time needed by the transmit wavefront to reach a point at location (x,y), the azimuth x=0 corresponding again to the center axis of the transmit beam. Let X be the azimuth of the received line with respect to the transmit beam axis. The delay applied to this received multiline to form a point of the image at depth Y is:

$$\text{Delay}(X,Y)=\text{propagation\_time}(X,Y)-\text{propagation\_time}(0,Y)$$

where propagation_time(0,Y) is the time to reach a point at the same depth but on-axis.

The functions amplitude(X,Y) and propagation_time(X,Y) may, for example, be obtained from a simulation of the transmit field. An appropriate way to compute the propagation time is to use the phase delay of the field from monochromatic simulation at several frequencies. The amplitude may be computed by averaging the amplitude of the field at several frequencies. In addition, a depth-dependent normalization can be applied to the weights. This multiplies all the weights at a given depth by a common factor. For example, the normalization can be chosen so that speckle regions have uniform brightness with depth. By varying the weights as a function of depth, it is possible to vary the size and shape (apodization) of the aperture dynamically with depth.

The amplitude and propagation time do not need to be derived from a simulation of the exact transmit characteristics used in the system. The designer may choose to use a different aperture size or a different apodization for example.

The echoes from each line are weighted by the multipliers 116a-116n and delayed by delay lines 118a-118n. In general, these delays will be related to the location of the transmit beam center to the receive line location as shown above. The delays are used to equalize the phase shift variance that exists from line to line for the multilines with differing transmit-receive beam location combinations, so that signal cancellation will not be caused by phase differences of the signals combined from different transmit apertures.

It will be appreciated that in a digital system the delay lines may be effected by storing the weighted multiline echo data in memory and reading the data out at later times which effect the necessary delay. Shift registers of differing lengths and clock signals may also be used to effect a digital delay, or an interpolating beamformer such as that described in the aforementioned U.S. Pat. No. 6,695,783 may be used. The delayed signals are combined by a summer 120 and the resultant signals are coupled to an image processor 122. The image processor may perform scan conversion or other processing to improve the displayed image. The resultant image is displayed on an image display 124.

In the system of FIG. 5 the delay lines 118 and summer 120 effect a refocusing of the signals received from the several receive multilines which are co-aligned in a given direction. The refocusing adjusts for the phase differences resulting from the use of different transmit beam locations for each multiline, preventing undesired phase cancellation in the combined signals. The weights 114 weight the contributions of the multilines in relation to the proximity of the transmit beam to the multiline location, giving higher weight to receive beams with higher signal-to-noise ratios. This results in an extended depth of field along each receive line and an enhanced penetration (improved signal-to-noise ratio) due to the combination of multiple samplings in each receive line direction.

This refocusing of co-aligned received multilines also causes a retrospective dynamic transmit focusing effect as explained with reference to FIG. 3. In this drawing four transmit beams 34 are transmitted by the transducer array 104, the transmit events being referred to as Tx1, Tx2, Tx3, and Tx4. Each transmit beam is transmitted in a different direction in the image field; in this example the transmit and receive beams are in parallel, and so each transmit beam originates from a different location (x dimension) along the transducer array. The energy of each transmission has a transmit beam profile generally indicated by the hourglass-shaped lines 30, which converges at a focal point indicated by arrow 32. Thus, each transmit beam is generated by its own transmit subaperture of the array. Following each transmission a receive line co-located with the transmit line is received and beamformed, and an additional receive beam 40 is received by the array transducer, each time at the same location (x direction) along the array. Two echo signal locations are marked by circles at the same depth y on each receive beam 40, one at a shallow depth and the other at a deeper depth. The receive beam for the first transmit event Tx1 is shown at 42. It is seen that for the first transmit event the receive beam 40 is offset to the right of the transmit beam 34 and since distance and time are equivalent in beamformation, the echoes received from the circled echo signal locations are located as shown on received beam 42 following beamforming.

In the second transmit-receive cycle of Tx2 the transmit beam 34 is laterally closer to the receive beam 40. This smaller offset results in the two circled echo signal locations being located closer to the focal point of the receive beam, as shown on the second receive beam 42'. In the third transmit-receive cycle of Tx3 the transmit beam is located laterally to the right of receive beam 40, separated by the same lateral distance as the Tx2 cycle. The echoes of the circled echo signal location are located as shown by the signals on receive beam 42". In the fourth transmit-receive cycle of Tx4 the transmit beam is located further to the right of the receive beam center, offset by the same distance as in the case of the first Tx1 cycle. The echoes of the circled echo signal location are located as shown by the signals on receive beam 42''', separated a greater distance from the receive beam focal point. The variation in the circled echo signal locations may be represented by curves 44 and 46 drawn across the four receive beams 42, 42', 42" and 42'''. This variation is corrected in retrospective dynamic transmit refocusing by applying a delay correction to the respective receive multilines before combining them. An exemplary delay curve profile is shown in U.S. Pat. No. 8,137,272 (Cooley et al.) for instance. When this compensating delay is applied by means of delay lines 118a-118n in FIG. 2 the circled echo locations are all reproduced at the same respective depths along the multilines 42-42''', as shown by circled depths 45 and 47, which are at corresponding receive line depths as shown by straight curves 54 and 56. The four corrected multilines may then be combined with weighting corresponding to the transmit-to-receive line offset to produce the final display scanline 50 with combined echo signals 52 and 58.

In accordance with the principles of the present invention the ultrasound system of FIG. 2 further includes a reverberation signal processor 100. The purpose of the reverberation signal processor is to identify the presence of reverberation signal artifacts in the echo signals received from the image field then, through a process of time reversal of the received reverb signal components back to virtual point sources located at the transmit beam focal points, estimate the phasing and weighting which would be used to generate the reverb signals if in fact they were to be transmitted and received. But no additional transmission and reception is employed. Instead, the estimated phases and weights are used to supplement the phases and weights used in the retrospective dynamic transmit refocusing, thereby obtaining the cancellation signals for reverberation signal artifacts in the received echo signals used for imaging.

This process begins by detecting the presence of reverberation signal artifacts in the received echo signals. This is done by operating on envelope-detected signals of the received multilines. In the implementation of FIG. 2 the initially beamformed signals produced by the multiline processors are envelope-detected by an envelope detector 92. A strong reflector which is the source of reverberations can be defined as any image pixel p(x,y) which is in the near field and close to the transducer, such as a pixel within the first half of the image, that is, $y \leq y_{max}/2$, where y indicates the image depth. The received signal from this strong reflector should also have a value which is greater than a threshold value of the intensity range, e.g., at least 80% of the maximum pixel intensity. For instance, if the pixel value range is 0 to 255, an 80% threshold value would be 204, assuring that any pixel suspected of containing the signal which causes the reverb has a substantially large amplitude. The intensity value of the suspected pixel should be at least two standard deviations greater than the mean intensity of a region of interest consisting of neighboring pixels, to make sure that the overall increased image gain is not causing the high intensity. Once these bright, high intensity pixels are identified in the image signals then beamformed r.f. lines (A-lines) corresponding to these high intensity points are investigated to find the strong echoes. In this example the beamformed A-lines are the detected multiline signals and pixel location p(x,y) corresponds to a signal at $A_i(t)$ where $A_i$ is the i'th A-line. For a linear array geometry the image depth y is directly related to the time $(t_e)$ when the echo occurs, $y=c_0 t_e/2$, where $c_0$ is the speed of sound in the imaging medium, and the line number i is the closest ultrasound beam to the lateral x-position of p. This may be expressed as the integer value of $i=((x-x_1)/\Delta x)+1$, where $x_1$ is the lateral position of the first A-line and $\Delta x$ is the distance between two consecutive A-lines. For a sector scan geometry, in which the beams are angularly dispersed and spatially originate at a common apex location, the scan conversion needs to be inverted first such that the depth r with respect to the scan origin given by $(x_0, y_0)$ is related to signal time of the echo, $r=\sqrt{(x-x_0)+(y-y_0)}=c_0 t/2$, and i is the integer value of $i=[(\tan((x-x_0)/(y-y_0))-\theta_1)/\Delta\theta]+1$ where $\theta_1$ is the angle of the first A-line and $\Delta\theta$ is the angle between two consecutive A-lines. The envelope of the rf-signal around $A_j(t)$ is calculated to find signals around the peak of $A_j(t)$, until the envelope drops down to half of the peak amplitude. Echoes with these characteristics are identified as the echoes of secondary transmissions, that is, reverberation artifacts.

Let $S_{ij}(t)$ indicate the received signals at the i'th receiver element following the j'th transmission $(Tx_j)$. $A_j$ is obtained by beamforming the signals $s_{ij}$ for all the receiving elements of the array, as indicated by the multiline processors 110a-110n in FIG. 2. The beamforming delays used to construct $A_j$ are used to identify the received signals such that if the signals from receiver i are delayed by $\phi$, and the echo time is calculated as $t_e$, then the signals around $t_e+\phi$ are responsible for the reverb. For this purpose there is direct communication between the unprocessed echo data from the probe and the reverb signal processor as shown in FIG. 2. The beamforming delays can be read in real time from the multiline processors or alternatively the same delays that are being used in the multiline processors can be also pre-loaded to the reverb signal processor. From a detected envelope of the signals, the signals on both sides of the peak $t_e+\phi$ are examined until the envelope amplitude drops down to half of the maximum amplitude. This echo location and signal levels are saved for the reverberation removal processing. These signals are referred to hereafter as $s^{rev}(t)$. The signals, $s^{rev}_{ij}(t)$ from all the receiving elements define the reverberation wavefront which is reflected from the transducer surface following the j'th transmission. This wavefront is generally complex (non-planar, not converging, not uniformly apodized), because the anatomical surfaces they reflect from are rarely flat.

Next, the reverberation signal processor performs a simulation of the reverb wave propagation, using the complex wavefront as input from the transducer side of the signal paths. The simulated waves 22' are propagated outward from the transducer array 104 towards the focal points 130 of the beams as shown in FIGS. 4 a) and b) for a sector geometry to decompose the wavefront into a number of virtual point sources. The amplitudes and arrival times of the propagated wavefront 22" are calculated for the focal points 130 of the beams as shown in FIG. 4 b). This is done by constructing a transmit-receive transform matrix $K_{TxRx}(t)$ using the signals $s^{rev}_{ij}(t)$ for the i'th element and j'th focused transmission:

$$K_{TxRx}(t) = \begin{bmatrix} s^{rev}_{11}(t) & s^{rev}_{12}(t) & K & s^{rev}_{1N}(t) \\ s^{rev}_{21}(t) & s^{rev}_{22}(t) & & s^{rev}_{2N}(t) \\ M & & O & M \\ s^{rev}_{M1}(t) & K & K & s^{rev}_{MN}(t) \end{bmatrix}$$

where M is the number of transducer elements and N is the number of focused transmissions. Each column of the $K_{TxRx}$ matrix represents the per-element received reverberation signal data following a focused transmission. Similarly the focused transmit matrix $K_{focus}(t)$ is constructed as $$K_{focus}(t) = \begin{bmatrix} s_{11}(t) & s_{12}(t) & K & s_{1M}(t) \\ s_{21}(t) & s_{22}(t) & & s_{2M}(t) \\ M & & O & M \\ s_{N1}(t) & K & K & s_{NM}(t) \end{bmatrix}$$

where $s_{ij}(t)$ denotes the signals being transmitted from each of M transducer elements for N focused transmissions. This computation is facilitated by the data line between the transmit beamformer 106 and the reverb signal processor as shown in FIG. 2. This matrix includes the delays and apodization weights associated with the transmit beamforming, which can be pre-loaded to the reverb signal processor. Both of these transformation matrices can also be represented in the frequency domain, $K_{TxRx}(\omega)$ and $K_{focus}(\omega)$, after Fourier transformation in the time dimension.

Any column of the matrix $K_{TxRx}$ can be left multiplied with the matrix $K_{focus}$ to simulate the propagation of the reverb signals to the focal points (virtual sources 130). Thus, $$V(\omega) = K_{focus}(\omega) K_{TxRx}(\omega)$$

where $V(\omega)$ is an N-by-N matrix whose columns represent the decomposition of reflecting reverberation echoes to the N virtual sources 130. The result is a complex (phase and amplitude) vector of N elements. This calculation can be repeated for each frequency $\omega$, typically by a Fourier transformation of n different frequencies corresponding to the Nyquist range of the signal sampling frequency, to decompose the reverberation wavefront from each transmit event into its virtual source components. An inverse Fourier transform of $V(\omega)$ is performed to get back to the arrival times and wave amplitudes at the focal points, which will serve as the delay times and weights for the virtual sources in the correction performed by the retrospective dynamic transmit focusing adjustment described above. FIG. 4 c) illustrates the virtual source points 130 re-positioned as a function of delay time $t_{delay}$, representing the delay times needed at the virtual source points for correction of the reverberation artifacts.

The received A-lines from the individual transmit event $Tx_j$, which have been stored in the line store 112, are combined (summed), after applying the standard retrospective dynamic transmit focusing corrections, to estimate the A-lines for the secondary (reverberation) transmit, $A^{rev}$ in the following equation:

$$A^{rev}(\omega) = [V(\omega)]^H A(\omega)$$

where superscript H indicates the Hermitian operator of a matrix. In this expression $A(\omega)$ indicates the column vector of an A line matrix expression after Fourier transformation and $A^{rev}$ indicates the approximations to the received and beamformed A-lines if the secondary transmit would have actually been transmitted. However, no physical beam transmission is actually done and the signals responsible for reverberation artifacts are approximately calculated by the inverse Fourier transform of $A^{rew}(\omega)$. Alternatively, per-channel data, instead of beamformed A-lines, from individual transmissions are used for retrospective dynamic transmit refocusing and are combined (summed) incorporating the weights and delays calculated to estimate the received signals for the secondary (reverberation) transmit. Finally, the estimated reverberation echo signals of the virtual secondary transmission are eliminated from the actual received signals by subtraction:

$$A^{corrected}(\omega) = A(\omega) - A^{rev}(\omega)$$

the corrected A-line is obtained by inverse Fourier transforming $A^{corrected}(\omega)$. Although the reverb cancellation process has been illustrated in the frequency domain, it can also be performed in the time domain. After the calculation of time delays and weights, the delays can be applied to the beamformed A-lines using bitshift techniques and weights can be multiplied with the delayed A-lines and the summation can be carried out in the time domain to obtain $A^{rev}(t)$. Finally, $A^{rev}(t)$ is subtracted from $A(t)$ to obtain $A^{corrected}(t)$.

The foregoing processing and reverberation artifact correction is illustrated sequentially in the flowchart of FIG. 5. The block 70 illustrates a method of creating an ultrasound image using the B mode transmit-receive sequence of a sequence of N transmit events (Tx #1, Tx #2, ... Tx #N), the echo data from which is used to create the ultrasound image. Each transmit event results in the reception of echo signals by each element (channel) in the transducer array, this per-channel (per-element) data being shown as Rcv #1 ... Rcv #N for the N transmit events. The echo data from each transmit event is beamformed into an A-line, thus forming A-L #1 ... A-L #N. In step 72 the set of echo data from Rcv #1 is analyzed to identify strong echoes responsible for reverberation, which can include envelope-detection of the rf signals, and searching for amplitude peaks which are greater than a threshold value and a number (e.g., two) of standard deviations greater than those of surrounding pixels. In step 74 a simulation of the propagation of an identified reverberation signal wavefront from the transducer toward the virtual point sources 130 is performed using the signal matrix equations given above, e.g., $V(\omega)$. An inverse Fourier transform of $V(\omega)$ yields the arrival times and signal amplitudes at the focal points which serve as the delay times and weights for reverberation correction as indicated in step 76. In step 78 the weights $w_i$ and delays $t_i$ are applied to the beamformed A-lines A-L #1 ... A-L #N from the N transmissions and in step 80 the weighted and delayed A-lines are summed to estimate the received reverberation signals (step 82). The method may further comprise a step 84 of eliminating the reverberation signals from the A-lines. This process is repeated for the Rcv #2 echo data set (step 88) to eliminate the reverberation signals from that set of data and after all data sets have been processed an image may be formed using the corrected A-lines (step 86).

It should be noted that an ultrasound system suitable for use in an implementation of the present invention, and in particular the component structure of the ultrasound system of FIG. 2, may be implemented in hardware, software or a combination thereof. The various embodiments and/or components of an ultrasound system, for example, the multiline processors, the weighting and delay circuits, the envelope detector and reverberation signal processor, and the image processor, and the components and controllers therein, also may be implemented as part of one or more computers or microprocessors. The computer or processor may include a computing device, an input device, a display unit and an interface, for example, for accessing the Internet. The computer or processor may include a microprocessor. The microprocessor may be connected to a communication bus, for example, to access a PACS system or the data network for importing training images. The computer or processor may also include a memory. The memory devices such as the line store 112 may include Random Access Memory (RAM) and Read Only Memory (ROM). The computer or processor further may include a storage device, which may be a hard disk drive or a removable storage drive such as a floppy disk drive, optical disk drive, solid-state thumb drive, and the like. The storage device may also be other similar means for loading computer programs or other instructions into the computer or processor.

As used herein, the term "computer" or "module" or "processor" or "workstation" may include any processor-based or microprocessor-based system including systems using microcontrollers, reduced instruction set computers (RISC), ASICs, logic circuits, and any other circuit or processor capable of executing the functions described herein. The above examples are exemplary only, and are thus not intended to limit in any way the definition and/or meaning of these terms.

The computer or processor executes a set of instructions that are stored in one or more storage elements, in order to process input data. The storage elements may also store data or other information as desired or needed. The storage element may be in the form of an information source or a physical memory element within a processing machine.

The set of instructions of an ultrasound system including those controlling the acquisition and processing of ultrasound images as described above may include various commands that instruct a computer or processor as a processing machine to perform specific operations such as the methods and processes of the various embodiments of the invention. The set of instructions may be in the form of a software program. The software may be in various forms such as system software or application software and which may be embodied as a tangible and non-transitory computer readable medium. Further, the software may be in the form of a collection of separate programs or modules such as ones executing the simulation and processing of the equations of the reverberation signal processor described above. The software also may include modular programming in the form of object-oriented programming. The processing of input data by the processing machine may be in response to operator commands, or in response to results of previous processing, or in response to a request made by another processing machine.

Furthermore, the limitations of the following claims are not written in means-plus-function format and are not intended to be interpreted based on 35 U.S.C. 112, sixth paragraph, unless and until such claim limitations expressly use the phrase "means for" followed by a statement of function devoid of further structure.

The invention claimed is:

1. A method for reducing reverberation signal artifacts in ultrasound images comprising:
receiving ultrasound echo signals along a plurality of multiline A-lines received in response to a common transmit event which contain reverberation signal artifacts;
processing the ultrasound echo signals by envelope detection;
detecting reverberation signal components in the ultrasound echo signals from an amplitude of envelope detected ultrasound signals in relation to a reference;
estimating time delays and amplitudes for reverberation signal correction from a simulation of transmission of reverberation signals to virtual point sources;
combining a plurality of the A-lines of the ultrasound echo signals using the estimated time delays and amplitudes to reduce reverberation signal components in the combined A-lines; and
forming an ultrasound image using the combined A-lines.

2. The method of claim 1, wherein receiving ultrasound echo signals further comprises transmitting a plurality of transmit events and receiving a plurality of multilines in response to each transmit beam.

3. The method of claim 2, wherein combining a plurality of multilines further comprises combining a plurality of multilines using time delays which refocus the multilines with respect to each other.

4. The method of claim 1, wherein detecting reverberation signals further comprises identifying ultrasound signal pixel amplitudes which are larger than a certain threshold and at least two standard deviations greater than surrounding pixels.

5. The method of claim 1, wherein the virtual point sources are located at focal depths of transmitted or received ultrasound beams.

6. The method of claim 1, wherein estimating time delays and amplitudes for reverberations signal correction further comprises estimating reverberation signal components from the received echo signals.

7. The method of claim 6, wherein the virtual point sources are located at focal depths of transmitted or received ultrasound beams; and
wherein the time delays and amplitudes are estimates from arrival times and amplitudes of simulated reverberation signal components at the virtual point sources.

8. The method of claim 6, wherein combining a plurality of A-lines of the ultrasound echo signals using the estimated time delays and amplitudes to reduce reverberation signal components further comprises subtracting estimated reverberation signal components from the received ultrasound echo signals.

9. The method of claim 7, wherein combining a plurality of A-lines further comprises combining a plurality of A-lines using refocusing delays to estimate A-lines containing reverberation artifacts.

10. A diagnostic ultrasound system for reducing reverberation signal artifacts in ultrasound images comprising:
multiline processors arranged to provide a plurality of A-lines by at least partially beamforming a plurality of received ultrasound echo signals which contain reverberation signal artifacts;

an envelope detector responsive to the plurality of A-lines and arranged to detect an envelope of each A-line, wherein each envelope detection includes an envelope amplitude detection;

a reverberation signal processor coupled to the envelope detector and arranged to detect reverberation signal components in the ultrasound echo signals from an amplitude of the envelopes, and to estimate time delays and amplitudes for reverberation signal correction from a simulation of transmission of reverberation signals to virtual point sources;

a combiner coupled to both the multiline processors and the reverberation signal processor and arranged to combine the plurality of A-lines of the ultrasound echo signals using the estimated time delays and amplitudes to reduce reverberation signal components in the combined A-lines; and an image processor arranged to form an ultrasound image using the combined A-lines.

11. The diagnostic ultrasound system of claim 10, wherein the reverberation signal processor is arranged to estimate time delays and amplitudes for reverberation signal correction by further calculating a product of a focused transmit signal matrix and a transmit-receive transformation matrix.

12. The diagnostic ultrasound system of claim 11, wherein the reverberation signal processor is arranged to estimate time delays and amplitudes for reverberation signal correction by further calculating an inverse Fourier transform of a complex reverberation wavefront matrix.

13. The diagnostic ultrasound system of claim 10, wherein the image processor is arranged to form an ultrasound image by forming an image from a plurality of multilines which have been refocused as a function of axes of their transmit beams.

* * * * *